(12) United States Patent
Furlan

(10) Patent No.: US 9,482,613 B2
(45) Date of Patent: Nov. 1, 2016

(54) INSTRUMENT AND METHOD FOR DETECTING ANALYTES

(75) Inventor: Alan Furlan, Zug (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 101 days.

(21) Appl. No.: 13/473,010

(22) Filed: May 16, 2012

(65) Prior Publication Data

US 2012/0295268 A1    Nov. 22, 2012

(30) Foreign Application Priority Data

May 16, 2011    (EP) .................................... 11166215

(51) Int. Cl.
- *G01N 21/64* (2006.01)
- *G01N 21/01* (2006.01)
- *G01N 21/25* (2006.01)

(52) U.S. Cl.
CPC ........ *G01N 21/6428* (2013.01); *G01N 21/255* (2013.01); *G01N 21/645* (2013.01); *G01N 21/253* (2013.01); *G01N 21/6486* (2013.01); *G01N 2021/6441* (2013.01); *G01N 2021/6471* (2013.01)

(58) Field of Classification Search
None
See application file for complete search history.

(56) References Cited

U.S. PATENT DOCUMENTS

| | | | |
|---|---|---|---|
| 3,636,366 A | 1/1972 | Sheldon | |
| 4,325,910 A * | 4/1982 | Jordan | ............................ 422/64 |
| 4,683,195 A | 7/1987 | Mullis et al. | |
| 4,683,303 A | 7/1987 | Pfaendler | |
| 4,800,159 A | 1/1989 | Mullis et al. | |
| 4,965,188 A | 10/1990 | Mullis et al. | |
| 5,316,726 A * | 5/1994 | Babson et al. | .................. 422/65 |
| 5,589,351 A | 12/1996 | Harootunian | |
| 5,830,134 A | 11/1998 | Caputo et al. | |
| 6,015,674 A | 1/2000 | Woudenberg et al. | |
| 6,144,448 A | 11/2000 | Mitoma | |
| 6,197,572 B1 | 3/2001 | Schneebeli | |

(Continued)

FOREIGN PATENT DOCUMENTS

| | | |
|---|---|---|
| DE | 1020060360171 | 1/2008 |
| EP | 1191336 | 7/1993 |

(Continued)

OTHER PUBLICATIONS

Kraeusche, Falko, "Announcing the family of Real-Time PCR platforms from Applied Biosystems," European Edition, Summer 2004, pp. 38-39, Issue 10.

*Primary Examiner* — Neil N Turk
(74) *Attorney, Agent, or Firm* — Pamela C. Ancona; M. Reza Savari

(57) ABSTRACT

The present disclosure provides instruments and methods for detecting an analyte which are capable of exciting a plurality of luminescence labels and detecting light emitted therefrom. The instrument includes a filter carrier adapted for carrying a plurality of filter portion pairs, each pair related to a luminescence label and comprising a first filter portion for transmitting excitation light, and a second filter portion for transmitting emitted light. The first filter portion of a pair comprises a second filter portion of another pair. Also, the filter portions are arranged such that a pair can be brought into an operative condition whereby a first filter portion is in the excitation beam path and a second filter portion is in the emission beam path. The filter carrier and beam paths may be moved with respect to each other by a moving mechanism so as to bring a pair into operative condition.

11 Claims, 6 Drawing Sheets

(56) References Cited

U.S. PATENT DOCUMENTS

| | | | |
|---|---|---|---|
| 6,569,631 | B1 | 5/2003 | Panloliano et al. |
| 6,814,934 | B1 | 11/2004 | Higuchi |
| 6,965,105 | B2 | 11/2005 | Oldham et al. |
| 6,982,431 | B2 * | 1/2006 | Modlin et al. ............ 250/573 |
| 7,008,789 | B2 | 3/2006 | Gambini et al. |
| 7,687,260 | B2 | 3/2010 | Gutekunst |
| 2002/0030044 | A1 | 3/2002 | Brown |
| 2003/0011772 | A1 | 1/2003 | Abe et al. |
| 2003/0038248 | A1 | 2/2003 | Maher et al. |
| 2004/0009586 | A1 | 1/2004 | Oldham et al. |
| 2006/0093254 | A1 | 5/2006 | Mozdy |
| 2006/0269922 | A1 | 11/2006 | Sagner et al. |
| 2007/0098594 | A1 | 5/2007 | Elkin et al. |
| 2007/0206187 | A1 | 9/2007 | Lundquist et al. |
| 2009/0218518 | A1 | 9/2009 | Schirr et al. |
| 2011/0039711 | A1 | 2/2011 | Howell et al. |
| 2012/0014835 | A1 | 1/2012 | Howell et al. |

FOREIGN PATENT DOCUMENTS

| | | |
|---|---|---|
| EP | 0902271 | 3/1999 |
| EP | 0953379 B1 | 11/1999 |
| EP | 0953838 | 11/1999 |
| EP | 1677097 A1 | 7/2006 |
| EP | 1681555 A1 | 7/2006 |
| EP | 1962085 A2 | 8/2008 |
| EP | 2081011 | 7/2009 |
| EP | 11166215 | 7/2014 |
| JP | 63298137 | 12/1988 |
| WO | 93/13423 | 7/1993 |
| WO | 00/71992 | 11/2000 |
| WO | 0248690 A1 | 6/2002 |
| WO | 03/098279 | 11/2003 |
| WO | 2004/024330 | 3/2004 |
| WO | 2010/079338 | 7/2010 |

* cited by examiner

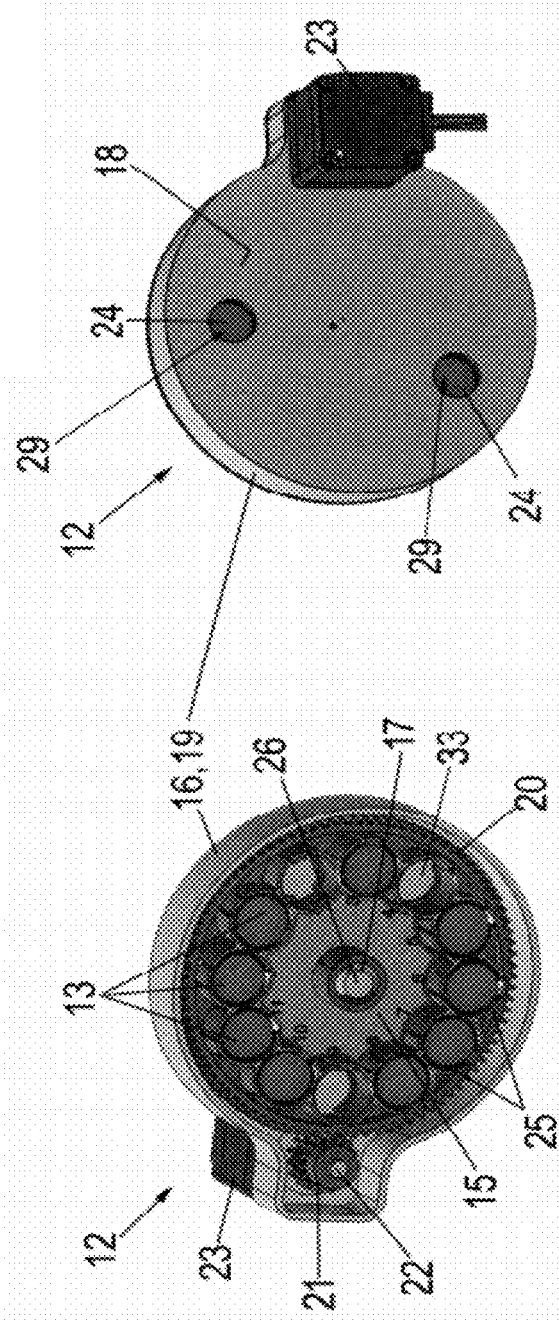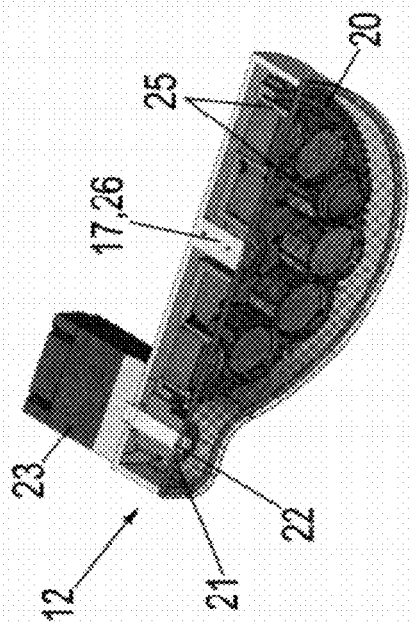
FIG. 2A
FIG. 2B
FIG. 2C

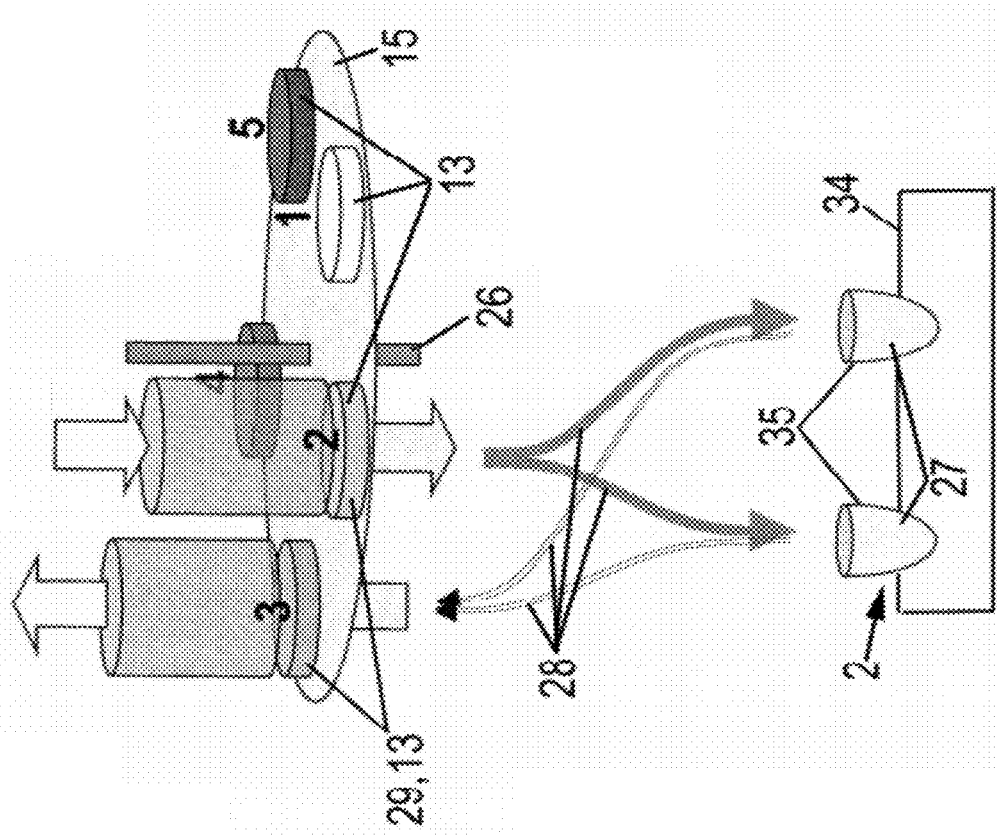
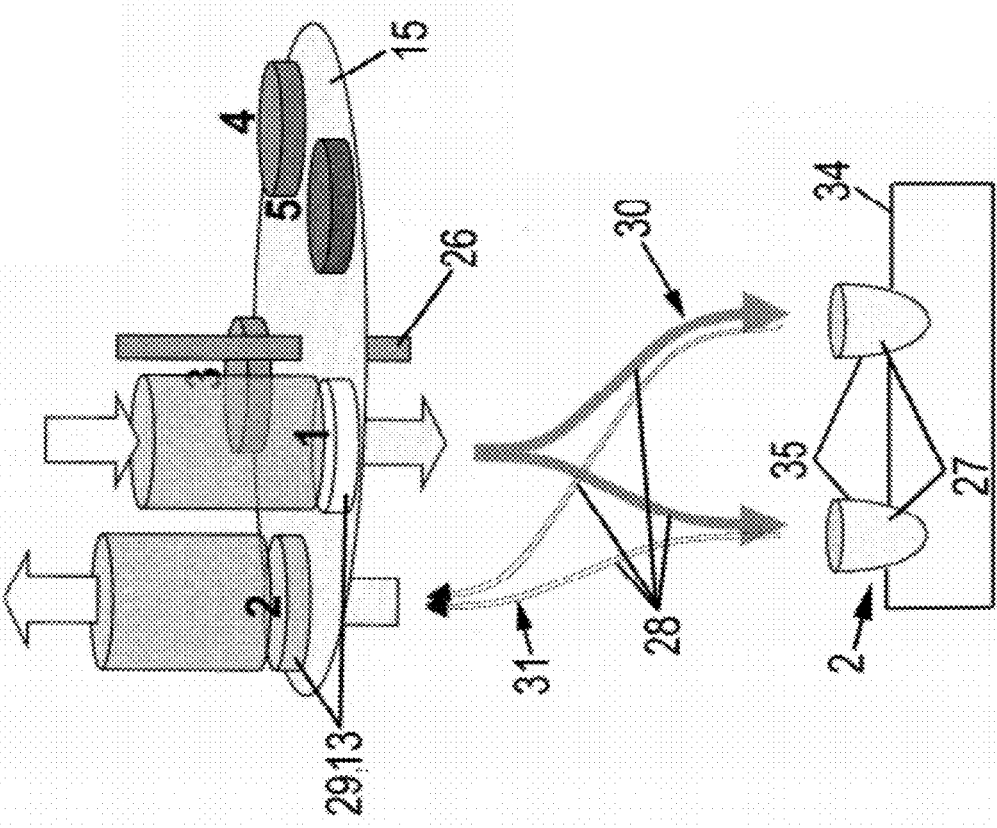
FIG. 4B
FIG. 4A

INSTRUMENT AND METHOD FOR DETECTING ANALYTES

PRIORITY CLAIM

This application claims the benefit of European Patent Application No. 11166215.1, filed May 16, 2011, the disclosure of which is hereby incorporated by reference in its entirety.

FIELD OF THE DISCLOSURE

The present disclosure relates to the fields of biochemical research, biochemical analytics, clinical diagnostics and clinical research in general. More specifically, the present disclosure relates to instruments and methods for the detection of analytes.

BACKGROUND

Known methods for detecting the presence of analytes in sample fluids include marking analytes with a label, such as a fluorescence dye, for optical detection of emitted light from the dyes (which may indicate the presence, amount or concentration of the analyte). Emission of light may occur, for example, in response to exposure to an excitation light or when a label is freed from a molecule.

In polymerase chain reaction (PCR), for example, in which target nucleic acids are replicated through a sequence of amplification steps (e.g., melting, annealing, and extension), nucleic acids may be combined with reagents containing fluorescence dyes which can react with the nucleic acids so as to mark the replicated nucleic acids with a dye. In real-time PCR, during each cycle of amplification, dye-marked replicated nucleic acids may be optically detected, for example, by exciting the dyes and measuring the fluorescence signal emitted in response to the excitation light. In some instances, the fluorescence signal obtained may be correlated to the amount of nucleic acid. Commercially available instruments may be used for performing real-time PCR and optical detection of the reaction products.

SUMMARY OF THE DISCLOSURE

According to embodiments of the instant disclosure, an automated low-cost instrument and method for the precise optical detection of analytes, such as reaction products of PCR, is provided. According to some embodiments, automated detection of analytes comprises measuring the emission of light of two or more luminescence labels for the detection of one or more analytes within a fluid sample.

According to a first aspect of the disclosure, a new instrument for the automated detection of at least one analyte in a sample is proposed. The instrument can be used to detect analytes by measuring light emitted by two or more luminescence labels indicating the analytes in response to excitation light. Stated more particularly, the instrument can, e.g., be used to detect at least two different analytes wherein each analyte is being indicated by one label, the labels of the various analytes being different with respect to each other. Otherwise, the instrument can, e.g., be used to detect one or more analytes, each of which being indicated by two or more labels which are different with respect to each other. By detecting the light emitted by the analyte-indicating labels, the presence and optionally amount or concentration of the analytes can be determined. The luminescence labels can, e.g., correspond to the analytes by reacting the analytes with one or more reagents containing the labels. Luminescence labels for use in the present disclosure can, e.g., be chosen from rhodamine, courmarine, cyanine dyes and derivates thereof. The luminescence labels can, e.g., be chosen as fluorescence dyes, wherein the specific value of the fluorescence signal obtained usually correlates to the amount of analyte contained in the sample.

In some embodiments, the instrument of the disclosure will particularly be useful for the optical (e.g. on-line) detection of PCR reaction products. For example, the instrument may be used for optically detecting the products of the PCR with hybridization probes, PCR with hydrolysis probes, PCR with interchelator dyes, real-time PCR with corresponding probes, various isothermal amplification methods with corresponding fluorescence reporters and melting analysis of DNA. Typical optical analyses are the detection of the presence/absence and optionally concentration of pathogens such as virus or bacteria in a sample, genotyping, measuring expression profiles, and many others.

According to the disclosure, as an excitation component, the instrument comprises at least one light source, capable of generating light for exciting two or more luminescence labels different with respect to each other. The at least one light source can, e.g., be chosen from a white light source such as, but not limited to, a halogen lamp and a white light emitting diode (LED), or from two or more quasi-monochromatic (multi-coloured) LEDs. The instrument further comprises an excitation beam path extending between the at least one light source and the sample (analyte) for propagation of the light generated by the at least one light source.

As a detection component, the instrument of the disclosure further comprises at least one detector capable of detecting light emitted from the sample, e.g., in response to excitation by the excitation light. The at least one detector can, e.g., be configured as charge coupled device (CCD), CMOS detector, camera, photomultiplier, photodiodes and many others. The instrument further comprises an emission beam path extending between the sample (analyte) and the detector for propagation of the light emitted from the sample.

As a light filtering component, the instrument of the disclosure further comprises one filter carrier carrying two or more pairs of filter portions, wherein each pair of filter portions is related to an individual luminescence label. Stated more particularly, each pair of filter portions is related to one luminescence label wherein different pairs of filter portions are related to different luminescence labels. Each pair of filter portions comprises one filter portion (in the following denoted as "first filter portion"), adapted to transmit excitation light generated by the at least one light source for exciting the related luminescence label and another filter portion (in the following denoted as "second filter portion"), adapted to transmit light emitted by the related label, wherein the first filter portion of one pair is the second filter portion of another pair. Furthermore, the filter portions are arranged in a manner that a respective one of the pairs of filter portions can be brought in a condition (in the following denoted as "operative condition") in which the first filter portion is arranged in the excitation beam path and the second filter portion is arranged in the emission beam path. In other words, the filter portions are arranged in a manner that one pair of filter portions can selectively be brought in operative condition while all other pairs of filter portions are not in operative condition, i.e. in a condition in which at least one filter portion thereof is not arranged in the excitation or emission beam paths (in the following denoted as "nonoperative condition"). Otherwise, each one of the pairs of filter portions can be brought in operative condition.

In some embodiments, in order to bring individual pairs of filter portions in operative condition, the filter carrier and the beam paths may be movable with respect to each other by means of at least one moving mechanism.

Stated more particularly, in the instrument of the disclosure, the moving mechanism can be embodied in a manner that the filter carrier is movable with respect to the stationary beam paths. Specifically, according to one embodiment of the disclosure, the moving mechanism is adapted to rotate the filter carrier in distinct positions with respect to the stationary beam paths so as to rotate a respective one of the pairs of first and second filter portions in operative condition, e.g. by equal rotation steps. According to one alternative embodiment, the moving mechanism is adapted to translate the filter carrier in distinct positions with respect to the stationary beam paths so as to translate a respective one of the pairs of first and second filter portions in operative condition, e.g., by equal translation steps. In these embodiments, it is preferred that the instrument comprises one carrier drive for moving the filter carrier in distinct positions relative to the excitation and emission beam paths. The carrier drive may be connected a controller, set up to control the activity of the carrier drive.

Otherwise, according to alternative embodiments of the disclosure, the moving mechanism is adapted to move the excitation and emission beam paths in distinct positions with respect to the stationary filter carrier so as to bring a respective one of the pairs of first and second filter portions in operative condition. This can be realized by moving and/or changing the direction of light guiding and/or light shaping and/or light directing elements such as light fibers, mirrors, prisms and the like.

Accordingly, some embodiments of the instrument of the disclosure may use only one (common) filter carrier for carrying the first and second filter portions which, e.g., can be moved by one carrier drive so that costs in producing the instrument can advantageously be saved. Otherwise, the first filter portions of one pair of filter portions can be used as second filter in another pair of filter portions. Hence, by double-using filter portions, costs in fabricating the instrument can advantageously be saved. Otherwise, different pairs of filter portions sharing one filter portion can very quickly be brought in operative condition, e.g., by moving the filter carrier by equal moving steps facilitating the moving mechanism.

As above-detailed, the samples containing the analytes can be liquid or dry samples. According to an embodiment related to liquid samples, the instrument can, e.g., comprise at least one mount for accommodating a sample carrier such as, but not limited to, a microplate comprising one or more wells, typically an array of wells, for containing liquid samples. According to an alternative embodiment related to dry samples, the instrument can, e.g., comprise at least one mount for accommodating a substrate with a surface comprising one or more analytes, e.g. covalently, attached to the surface in discrete regions, such as, but not limited to, groups of oligonucleotides having similar or different nucleotide sequences.

In some embodiments of the instrument of the disclosure, the filter carrier may carry a plurality of filter portions. According to one embodiment, the filter carrier is provided with a plurality of distinct filter portions. For that purpose, the filter carrier may include a plurality of seats for (e.g. removably) fixing the filter portions. Specifically, the first and second filter portions of one pair of filter portions can, e.g., be separated by at least one seat that can be a blank seat (i.e. without filter portion) or can be provided with a filter portion of another pair of filter portions. Hence, neighbouring filter portions can belong to different pairs of filter portions.

According to an alternative embodiment, the filter carrier is carrying a one-piece filter comprised of the first and second filter portions, wherein the one-piece filter can have a continuous or discontinuous, i.e. discrete, transmission spectrum. Specifically, the one-piece filter may, e.g., include a plurality of distinct filter portions serially arranged with respect to each other.

According to an embodiment, the filter carrier is provided with at least one opaque region, adapted to inhibit the transmission of light emitted by the sample that is arranged in a manner to be brought in the emission beam path, e.g., by moving the filter carrier. The opaque region can be, e.g., be used to calibrate the instrument.

According to a second aspect, a new method for detecting the presence and optionally amount or concentration of at least one analyte in a sample or on a pad is proposed. The method comprises a step of generating excitation light propagating along an excitation beam path towards said sample. It comprises a further step of detecting light emitted from the sample in response to the excitation light, propagating along an emission beam path. It comprises a further step of moving one (first) pair of first and second filter portions related to one luminescence label and said beam paths with respect to each other so that the (first) pair is in an operative condition in which the first filter portion thereof, adapted to transmit excitation light for exciting the related luminescence label, is arranged in the excitation beam path and the second filter portion thereof, adapted to transmit light emitted by the related luminescence label, is arranged in the emission beam path. It comprises a further step of moving another (second) pair of first and second filter portions related to another luminescence label and the beam paths with respect to each other so that the another (second) pair of filter portions is in the operative condition, wherein the first filter portion of the one (first) pair of filter portions is the second filter portion of the another (second) pair of filter portions.

According to a preferred embodiment, a filter carrier carrying the first and second filter portions is rotated in distinct rotating positions relative to the excitation and emission beam paths kept stationary so as to move a respective one of the pairs of filter portions in the operative condition. Alternatively, the filter carrier carrying the first and second filter portions is translated in distinct translating positions relative to the excitation and emission beam paths kept stationary so as to translate a respective one of the pairs of filter portions in the operative condition. It can especially be preferred to move the filter carrier by equal moving, i.e., rotating and translating, respectively, steps.

According to an alternative embodiment, the excitation and emission beam paths are moved in distinct positions with respect to the first and second filter portions kept stationary so as to bring a respective one of the pairs of first and second filter portions in operative condition.

According to a third aspect, a new system for analyzing a sample by detecting the presence and optionally amount or concentration of at least one analyte is proposed. The system comprises an instrument for detecting the presence of at least one analyte in a sample as above-detailed. Stated more particularly, the system comprises a temperature-controlled block for heating the sample, e.g., for thermo-cycling the sample. The system further comprises at least one light source capable of generating light for exciting two or more luminescence labels and an excitation beam path extending between the light source and the sample for propagation of the excitation light. The system further comprises at least one detector capable of detecting light emitted from the sample, e.g., in response to the excitation light, and an emission beam path extending between the sample and the detector for propagation of the emitted light. It further comprises one filter carrier carrying two or more pairs of filter portions, wherein each pair is related to one luminescence label comprising a first filter portion, adapted to transmit excitation light for exciting the related luminescence label, and a second filter portion, adapted to transmit light emitted by the related luminescence label, wherein the first filter portion of one pair is the second filter portion of another pair. In the system, the filter carrier is movable with respect to the excitation and emission beam paths by at least one moving mechanism so as to bring a respective one of the pairs of filter portions in an operative condition in which the first filter portion is in the excitation beam path and the second filter portion is in the emission beam path. The system further comprises one carrier drive for moving the filter carrier in distinct positions relative to the excitation and emission beam paths, and a controller set up to control activity of the carrier drive in a manner to move a respective one of the pairs of first and second filter portions in operative condition.

Further, according to some exemplary embodiments of the present disclosure, an instrument for detecting an analyte in a sample is provided. According to some embodiments, the instrument comprises a light source capable of generating an excitation light for exciting a plurality of luminescence labels, an excitation beam path extending between said light source and said sample for propagation of said excitation light, a detector capable of detecting an emission light emitted from said one of said plurality of luminescence labels, an emission beam path extending between said sample and said detector for propagation of said emission light, a filter carrier comprising a plurality of filter portion pairs, each pair relating to one of said plurality of luminescence labels and comprising a first filter portion, adapted to transmit said excitation light for exciting the related luminescence label, and a second filter portion, adapted to transmit said emission light emitted by said related luminescence label, said first filter portion of one of said plurality of pairs comprising said second filter portion of another of said plurality of pairs, said filter portions being arranged in a manner such that one of said plurality of pairs can be brought into an operative orientation in which said first filter portion is in said excitation beam path and said second filter portion is in said emission beam path, said filter carrier and said beam paths being movable with respect to each other by a moving mechanism so as to bring one of said plurality of pairs in said operative orientation, and a mount configured for one of holding a sample carrier and accommodating a substrate. In some embodiments, the luminescence labels are not chemically (or otherwise) bound to the analyte, whereas in other embodiments the luminescence labels are bound to the analyte.

According to other exemplary embodiments of the instant disclosure, a method for detecting an analyte in a sample is provided. In some embodiments, the method includes the steps of generating an excitation light, said excitation light propagating along an excitation beam path towards said sample, detecting an emission light emitted from a luminescence label, said emission light propagating along an emission beam path, moving a first pair of a plurality of pairs of filter portions comprising a first and a second filter portion related to said luminescence label and said excitation and emission beam paths with respect to each other so that said pair of filter portions is in an operative orientation in which said first filter portion, adapted to transmit said excitation light for exciting said related luminescence label, is in said excitation beam path and said second filter portion, adapted to transmit said emission light emitted by said related luminescence label, is in said emission beam path, moving a second pair of said plurality of pairs of filter portions relating to a second luminescence label, and moving said beam paths with respect to each other so that said second pair is in said operative orientation, wherein the first filter portion of said first pair of filter portions comprises the second filter portion of the second pair of filter portions.

In yet other embodiments of the instant disclosure, a system for analyzing a sample is provided. The system, according to various embodiments, includes a temperature-controlled block for heating said sample, a light source capable of generating an excitation light for exciting at least one of a plurality of luminescence labels, an excitation beam path extending between said light source and said sample for propagating said excitation light, a detector capable of detecting an emission light emitted from one of said plurality of luminescence labels, an emission beam path extending between said sample and said detector for propagating said emission light and a filter carrier carrying two or more pairs of filter portions, each pair of filter portions being related to one luminescence label and comprising a first filter portion, adapted to transmit excitation light for exciting said related luminescence label, and a second filter portion, adapted to transmit said emission light emitted by said related luminescence label, wherein said first filter portion of one pair is said second filter portion of another pair, said filter carrier being movable with respect to said excitation and emission beam paths by a moving mechanism so as to bring one of said pairs in an operative orientation in which said first filter portion is in said excitation beam path and said second filter portion is in said emission beam path. Additionally, in some embodiments the system includes a carrier drive for moving said filter carrier in distinct positions relative to said excitation and emission beam paths, a controller configured to control activity of said carrier drive in a manner to move one of said pairs of said first and second filter portions in said operative orientation, and a mount for at least one of holding a sample carrier and accommodating a substrate.

Even further, in some embodiments of the present disclosure an instrument for detecting at least one analyte is provided. The instrument may include at least one light source, capable of generating excitation light for exciting two or more luminescence labels, an excitation beam path extending between said light source and said analyte, at least one detector, capable of detecting light emitted from said luminescence label, an emission beam path extending between said analyte and said detector, one filter carrier carrying two or more pairs of filter portions, each pair being related to one luminescence label and comprising a first filter portion for transmitting excitation light and a second filter portion for transmitting emitted light. The first filter portion of one pair is said second filter portion of another pair, and wherein said filter portions are arranged in a manner that a respective one of said pairs can be brought in an operative condition in which said first filter portion is in said excitation beam path and said second filter portion is in said emission beam path, and wherein said filter carrier and said beam paths are movable with respect to each other by at least one moving mechanism so as to bring a respective one of said pairs in said operative condition. In a method for detecting at least one analyte, one pair of filter portions is moved in said operative condition and another pair of filter portions is moved in said operative condition, wherein the first filter portion of the one pair of filter portions is the second filter portion of the another pair of filter portions.

The above-described embodiments of the various aspects of the disclosure may be used alone or in any combination thereof without departing from the scope of the disclosure.

BRIEF DESCRIPTION OF THE DRAWINGS

The features and advantages of this disclosure, and manner of attaining them, will become more apparent and disclosure itself will be better understood by reference to the following description of embodiments of the disclosure taken in conjunction with the accompanying drawings, which are incorporated in and constitute a part of the specification. In the drawings, similar structures are referred to by like numerals throughout the various embodiments.

FIGS. 2A-2C are perspective drawings illustrating a rotatable filter arrangement of the instrument of FIG. 1;

FIGS. 4A-4B are schematic drawings illustrating an exemplary method using the rotatable filter arrangement of FIGS. 2A-2C;

Figure 1:
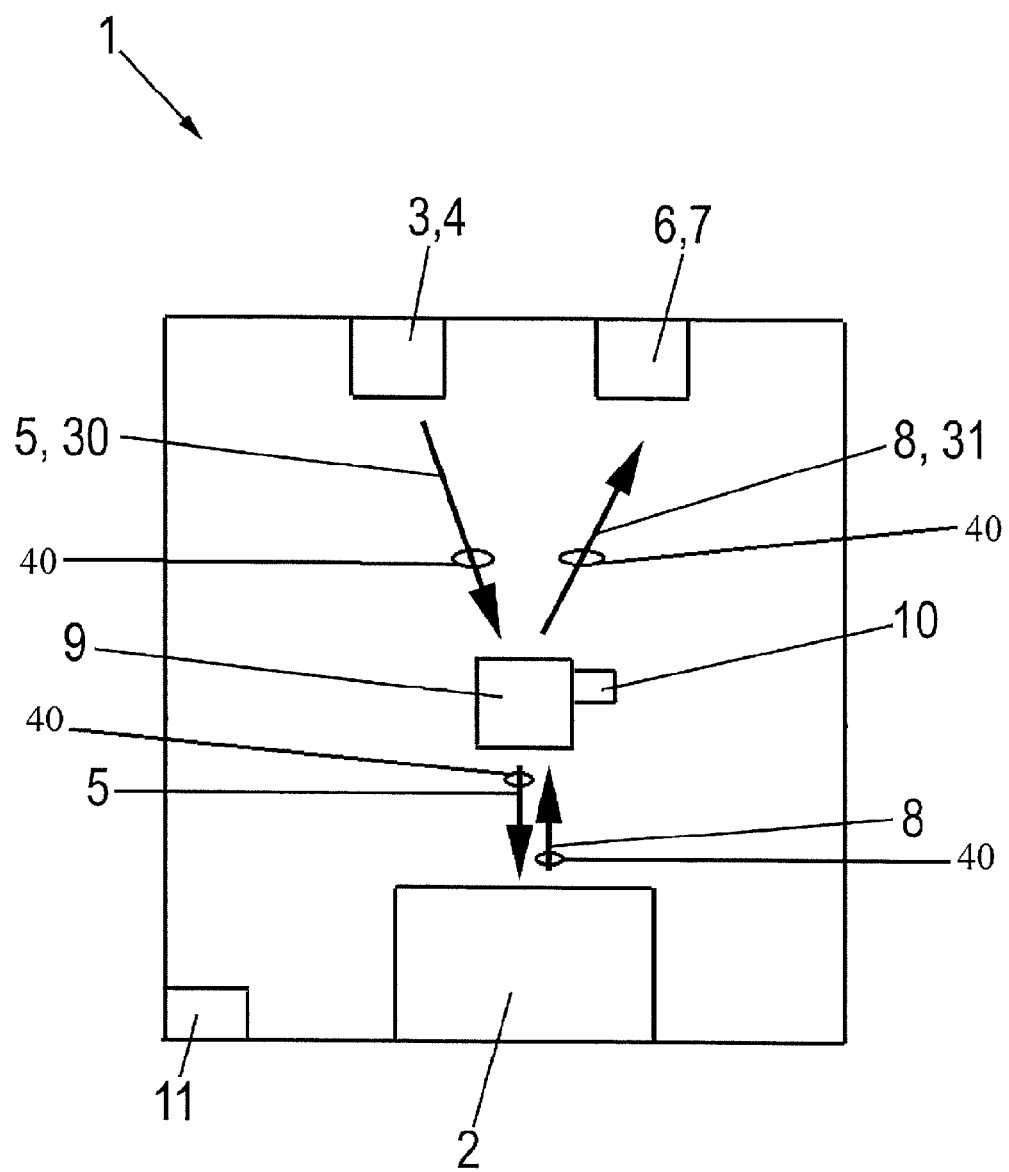
FIG. 1 is a schematic drawing illustrating an embodiment of the instrument of the disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Very generally, embodiments of the instrument of the instant disclosure are useful for detecting the light emitted by two or more labels different with respect to each other by having different excitation and emission peaks. As used herein, the term "peak" refers to the wavelength or range of wavelengths causing a maximum intensity of light emitted by the related label. The labels are chosen in a manner that the excitation peak of one label at least approximately corresponds to the emission peak of another label. In some embodiments the labels may be bound (e.g., chemically or otherwise) to the analyte, whereas in other embodiments the labels are not bound to the analyte.

As used herein, the term "analyte" refers to any substance the presence and optionally amount or concentration of which can be determined by measuring the emission of light of at least one luminescence label related thereto.

As used herein, the term "sample" refers to any substance in which the analyte can be contained. Samples can, e.g., be liquid samples or dry samples. For example, analytes can be contained in chemical fluids which can be subject to one or more chemical analyses and assays, e.g., drug interaction screening, environmental analysis, identification of organic substances, etc. Analytes can, e.g., be contained in biological fluids such as body fluids, e.g., blood, serum, urine, saliva, cerebrospinal fluid etc. which can be subject to one or more analyses and assays in medical and pharmaceutical research and clinical diagnosis which may involve in-vitro amplification techniques, e.g., based on the polymerase chain reaction (PCR) or any other reaction of the nucleic acid amplification type. Analytes can, e.g., be contained in pre-processed body fluids such as extracts of body fluids containing target nucleic acids used as starting materials, e.g., for the PCR. Analytes can also be contained in any other fluid of interest. For example, analytes can be nucleic acids or segments thereof, proteins, antibodies, cells and many others.

Referring to FIG. 1, an instrument for detecting the presence and optionally the amount or concentration of at least one analyte, is generally represented as reference numeral 1. According to the instant disclosure, instrument 1 may be used to optically detect reaction products obtained by thermally cycling liquid reaction mixtures of nucleic acids and one or more reagents through a series of temperature excursions. Instrument 1 may be used to detect reaction products of PCR, for example real-time PCR, or any other reaction of the nucleic acid amplification type. Instrument 1 may be used for the optical on-line detection of various reaction products.

Remaining with FIG. 1, instrument 1 may include various components as detailed in the following description which may comprise both functional and structural entities for detecting the presence/absence and, in some case the amount or concentration of at least one analyte. For example, as illustrated in FIG. 1, instrument 1 may include an analyte region 2 for containing the one or more analytes, the presence or absence of which may be optically detected by means of at least two luminescence labels.

As shown in FIG. 1, instrument 1 may further include an excitation arrangement 3 provided with at least one light source 4 capable of generating light adapted for exciting at least two luminescence labels contained in the analyte region 2. Light source 4 may be configured as a white light source such as a halogen lamp or a white light emitting diode (LED) for example. In some embodiments, multiple coloured LEDs having different wavelengths or ranges of wavelengths may be used. According to embodiments of the instant disclosure, the excitation arrangement 3 generates excitation light 30 for exciting two or more luminescence labels contained in the analyte region 2. As depicted in FIG. 1, excitation light 30 propagates along an excitation beam path 5 extending between the excitation arrangement 3 and the analyte region 2 passing through a filter arrangement 9 provided with two or more pairs of filter portions as described in more detail below. An excitation optics (not further detailed in FIG. 1) may be used to transmit the excitation light 30 to the analyte region 2 via the excitation beam path 5.

Continuing with FIG. 1, instrument 1 may include a detection arrangement 6 having at least one detector 7 capable of detecting light 31 emitted from the analyte region 2, for example in response to the excitation light 30. Detector 7 may include one or more light-sensitive elements for optically detecting light 31 emitted from analyte region 2. According to various embodiments, detector 7 can be embodied as a lateral-resolving detector like a charge coupled device (CCDs) and a CMOS detector, a linear-array detector movable for scanning, and a two-dimensional-array sensor such as a camera, for example. As depicted in some embodiments of instrument 1, light 31 emitted from analyte region 2 propagates along an emission beam path 8 extending between analyte region 2 and detection arrangement 6 passing through filter arrangement 9. An emission optics (not further detailed in FIG. 1) may be used to transmit light emitted from the analyte region 2 via emission beam path 8 to detector 7.

According to various embodiments, excitation and/or emission beam paths 5, 8 may include one or more light guiding and/or light shaping and/or light directing elements such as, but not limited to, lenses 40 and planar or bent mirrors and/or one or more light separating elements such as, but not limited to, transmission gratings, reflective gratings and prisms in order to transmit excitation light 30 from excitation arrangement 3 to analyte region 2 and to detect light 31 emitted by the analyte region 2 by the detection arrangement 6.

Remaining with FIG. 1, filter arrangement 9 is depicted having two or more pairs 29 of filter portions 13. Filter arrangement 9 may be movable with respect to beam paths 5, 8 by means of a moving mechanism 32 (not further detailed in FIG. 1). According to some embodiments, moving mechanism 32 may be coupled to at least one drive 10 for moving the filter arrangement 9 into distinct positions relative to the excitation and emission beam paths 5, 8.

As depicted in FIG. 1, instrument 1 may further include a controller 11 set up to control the activity of the various components of instrument 1. In some embodiments, controller 11 may be configured as a programmable logic controller running a machine-readable program provided with instructions for performing operations for detecting the presence/absence, and optionally the amount or concentration, of one or more analytes contained in analyte region 2. For example, in some configurations, controller 11 may receive information from, and generate and transmit control signals to, the components of instrument 1 requiring control such as drive 10, at least one light source 4, and at least one detector 7. According to some embodiments of the present disclosure, electric lines (not shown) may be used for transmitting the signals.

With reference to FIGS. 2A-2C, illustrative embodiments of filter arrangement 9 (FIG. 1) according to the present disclosure are presented. As depicted, filter arrangement 9 (FIG. 1) may comprise a filter unit 12 illustrated by a front perspective view (FIG. 2A), a back perspective view (FIG. 2B) and a sectional perspective view. As shown, filter unit 12 may include a plurality of distinct first and second filter portions 13 fixed to a rotatable carrier or filter wheel 15. Filter wheel 15 may be rotatably mounted to a wheel hub 17 protruding from a disk-like base portion 18 of a wheel casing 16. According to some embodiments, wheel casing 16 may be comprise base portion 18 and a rim portion 19 surrounding base portion 18 so as to form a trough accommodating filter wheel 15. As shown in FIG. 2A, filter wheel 15 may include an outer toothing 20 which is in meshing engagement with a pinion 21. According to the illustrative embodiment, pinion 21 is driven by a shaft 22 of an electric motor 23 fixed to base portion 18 of wheel casing 16. Accordingly, filter wheel 15 can be rotated around central wheel hub 17 thereby defining a spin axis 26 so as to rotate filter portions 13.

As illustrated in FIG. 2B, base portion 18 of wheel casing 16 may be provided with two openings 24, (for example, a first opening 24 and a second opening 24), which in radial direction have an equal radial distance from central wheel hub 17 or spin axis 26. In some embodiments of the instant disclosure, in circumferential direction the openings 24 are arranged in a manner that the radii passing through the openings 24 enclose an angle of 150°. According to embodiments of instrument 1, first opening 24 is located in excitation beam path 5 and second opening 24 is located in emission beam path 8.

As illustrated in FIGS. 2A and 2C, filter wheel 15 may be provided with a plurality of seats 25, the diameter of which at least approximately correspond to the diameter of openings 24. While a number of twelve seats 25 is shown for the purpose of illustration only, those of skill in the art will appreciate that any other number of seats 25 can be envisaged according to the specific demands of the user. Also, while both seats 25 and opening 24 are shown as being circular in shape, other shapes may be utilized. As illustrated, seats 25 are circumferentially arranged with respect to each other so as to have an equal radial distance with respect to central wheel hub 17 or spin axis. According to some embodiments, the radii passing through two adjacent seats 25 may enclose an angle of 30°. Each seat 25 may be loaded with a filter portion 13 and seats 25 may be adapted for removably fixing filter portions 13 by means of a fixation mechanism such as, but not limited to, a catch mechanism, clamp mechanism or the like. The arrangement of seats 25 and openings 24 allows for two seats 25, the radii of which enclose an angle of 150°, to be brought into a position to simultaneously overlap openings 24. Hence, a first filter portion 13 and a second filter portion 13(e.g., a pair 29 of first and second filter portions 13) may be positioned in the excitation and emission beam paths 5, 8 while each other filter portion 13 is outside the excitation and emission beam paths 5, 8.

Figure 3:
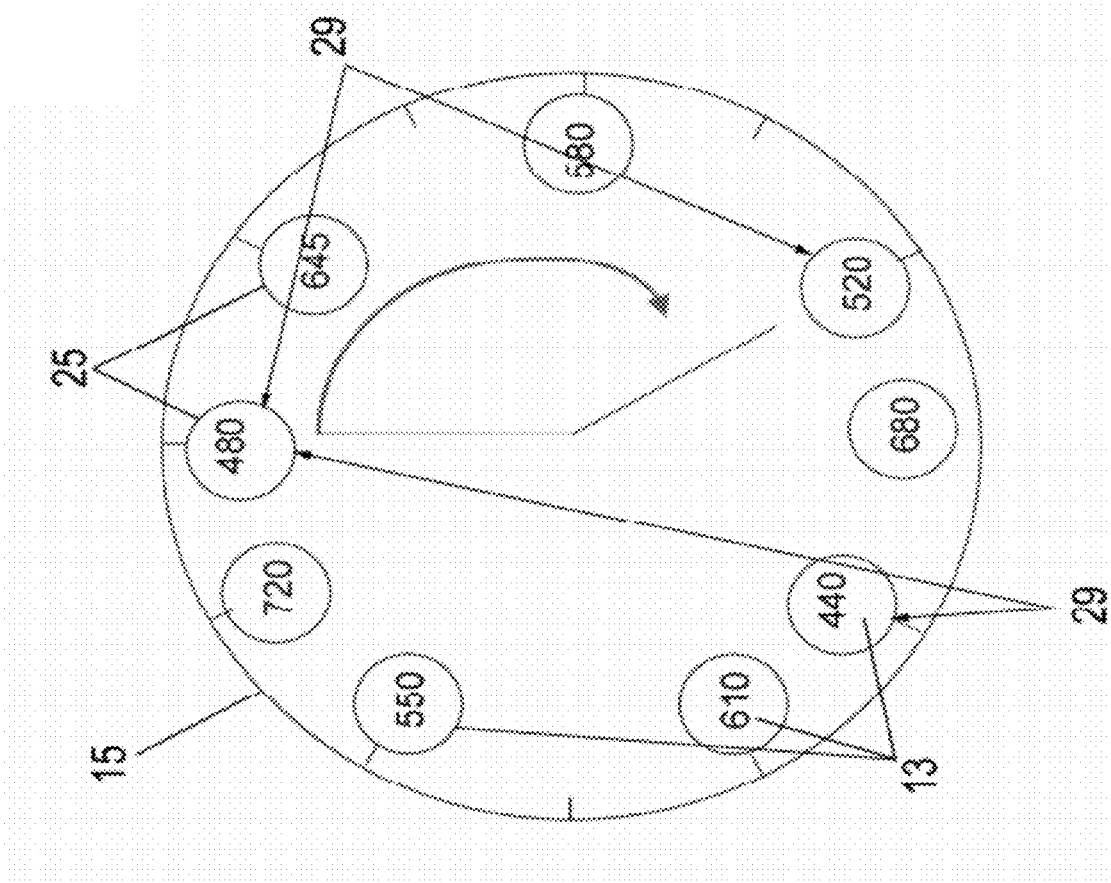
FIG. 3 is a schematic drawing illustrating various discrete filter portions of the rotatable filter arrangement of FIGS. 2A-2C.

Referring to FIG. 3, an exemplary loading of filter wheel 15 with various discrete filter portions 13 is shown. As shown, filter portions 13 may relate to a number of eight fluorescence labels or dyes as indicated in the table of FIG. 3. These dyes may differ both in their excitation peaks and emission peaks as indicated by the wavelength (nm) for a maximum intensity (central wavelength) of the excitation spectrum (Ex) and emission spectrum (Em). These dyes may be selected in a manner that the Stokes shift of the dyes is rather similar with respect to each other, wherein the emission peak of one dye at least approximately corresponds to the excitation peak of another dye. For example, the dye "Cyan 500" has an emission peak of 480 nm corresponding to the excitation peak of the dye "FAM". Also, the dye "FAM" has an emission peak of 520 nm corresponding to the excitation peak of the dyes "HEX, VIC," and so on.

As illustrated, filter wheel 15 may be loaded with filter portions 13 in a manner that one pair 29 of first and second filter portions 13, the radii of which may enclose an angle of 150°, relate to one dye. For example, for each dye filter wheel 15 may include one pair 29 of first and second filter portions 13, the radii of which may enclose an angle of 150°, wherein the first filter portion 13 is adapted to transmit the excitation light and the second filter portion 13 is adapted to transmit light emitted by the dye in response to the excitation light. Accordingly, filter wheel 15 may include a number of eight pairs 29 of first and second filter portions 13 each of which being related to an individual dye, wherein each first filter portions 13 of one pair 29 corresponds to the second filter portion 13 of another pair 29 or vice versa so as to double-use one filter portion 13 for both pairs 29.

In the following, for the ease of explanation only, the position of the various pairs 29 of filter portions 13 of the filter wheel 15 are denoted by referring to a clock's notation as indicated in FIG. 2A. According to the illustrated embodiment of the present disclosure, a pair 29 of first and second filter portions 13 of "Cyan 500" is located at 7 and 12 o'clock, a pair 29 of first and second filter portions 13 of "FAM" is located at 12 and 5 o'clock, a pair 29 of first and second filter portions 13 of "HEX, VIC" is located at 5 and 10 o'clock, a pair 29 of first and second filter portions 13 of "NED, TAMRA" is located at 10 and 3 o'clock, a pair 29 of first and second filter portions 13 of "RED610, ROX" is located at 3 and 8 o'clock, a pair 29 of first and second filter portions 13 of "JA270, CY5, Red640" is located at 8 and 1 o'clock, a pair 29 of first and second filter portions 13 of "Red670" is located at 1 and 6 o'clock, and a pair 29 of first and second filter portions 13 of "Red710, CY5.5" is located at 6 and 11 o'clock.

As illustrated, individual pairs 29 of first and second filter portions 13 may have radii enclosing an angle of 150° and thus can selectively be brought in overlap with openings 24 by rotating filter wheel 15 by 150° or multiples thereof. Each of the filter portions 13 may be used for the filtering the excitation light of one dye and the light emitted from another dye. As a result, according to the illustrative embodiment, eight dyes can be excited and light emitted therefrom can be detected by turning the filter wheel 15 eight times by 150° (i.e., eight one-step turns). Accordingly, cost for the production of filter unit 12 and time for detecting the presence of analytes involving the use of two or more dyes can advantageously be saved. While a number of eight pairs 29 related to eight dyes of filter portions 13 is shown for the purpose of illustration only, those of skill in the art will appreciate that any other number of dyes and pairs 29 of filter portions 13 may be utilized according to the specific needs or desires of the user. Additionally, while adjacent seats 25 are depicted as arranged to enclose an angle of 30°, those of skill in the art will appreciate that other angles may be utilized according to the specific needs or desires of the user, wherein the angle between the openings 24 will also be adapted correspondingly. Further, according to some embodiments provided herein, because the first and second filter portions 13 (of one pair 29 of filter portions) are separated by (for example, three seats 25 which are either blank seats or provided with filter portions 13 belonging to other pairs 29 of filter portions), the exciting and emitted light is spatially separated from each other so as to avoid crosstalk.

Referring again to FIG. 2A, filter unit 12 depicts that, the filter wheel 15 may be open at the seats 25 so that light can pass through the seats 25 in case filter portions 13 are in overlap with the base portion openings 24. Also illustrated, at 2, 4, and 9 o'clock, for example, there are blank seats 25. According to some embodiments, blank seats 25 may be closed by a cover (not illustrated) so as to block light to pass therethrough to thereby form opaque regions 33 which may be used to calibrate instrument 1, for example.

With reference to FIGS. 4A-4B, an exemplary method for detecting the presence, and in some instances the amount or concentration, of at least one analyte by measuring emission of light of dyes using instrument 1 having filter wheel 15 (of FIGS. 2 to 3) is depicted. In FIGS. 4A-4B, for the purpose of ease of illustration only, the filter wheel 15 is shown to be provided with a number of five filter portions 13, although as explained herein the number of filter portions 15 may vary. Two samples 27 containing the analyte may be located in the analyte region 2 on a mount 34 supporting sample vessels 35 containing the samples 27. Both excitation and emission fibers 28 may guide light 30, 31 towards or away from the samples 27.

FIG. 4A illustrates a first rotating position of filter wheel 15 in which one pair 29 of filter portions 13 related to one dye, e.g. Cyan 500, is in operative position in which the first and second filter portions 13 are in overlap with the openings 24. Accordingly, first filter portion 13, adapted to transmit and filter excitation light 30 having an excitation peak of 440 nm, for example, is located in the excitation beam path 5 so that the dye can be excited by light 30 directed towards the samples 27 via the excitation fibers 28. Also illustrated, second filter portion 13, adapted to transmit and filter light 31 emitted by samples 27 in response to excitation light 30 (having an emission peak of 480 nm), is located in emission beam path 8 so that light 31 collected by emissions fibers 28 may be detected by detector 7. According to some embodiments, the output of emission fibers 28 may be imaged onto a camera chip and detected with spatial resolution. In some embodiments, the central wavelength of second filter portion 13 may be about 40 nm longer than that one of first filter portion 13 corresponding to a typical Stokes shift of fluorescent dyes.

With reference to FIG. 4B, turning filter wheel 15 to a second rotating position brings another pair 29 of filter portions 13, related to another dye different from the former dye into an operative position, wherein second filter portion 13 of the former dye is the first filter portion 13 of the present dye or vice versa. Accordingly, the first filter portion 13 adapted to transmit and filter light 30 having an excitation peak of 480 nm is located in excitation beam path 5 so the dye may be excited. Additionally illustrated, second filter portion 13, adapted to transmit and filter light 31 emitted by samples 27 (in response to the excitation light having an emission peak of 520 nm, for example), is located in emission beam path 8 such that emitted light may be detected by the detector 7. Accordingly, light 31 emitted by two dyes may readily be detected by detector 7 involving a single or one-step turn of filter wheel 15. As such, according to various embodiments of the instant disclosure, by rotating filter wheel 15 a number of one-step turns, a same number of dyes may be excited and light emitted therefrom can be detected in response to the excitation light.

Furthermore, filter wheel 15 can be brought in a rotating position in which blank seats 25 provide forming an opaque region 33 are in overlap with the openings 24 so as to inhibit light transmission towards the analyte region 2 and/or towards the detector 7 (by a cover on the blank seats 25 or providing for closed blank seats 25 as above-described). Accordingly, detector 7 may be tested for the detection of light not originating from the analyte region 2 so as to improve the reliability of the detection results.

Figure 5:
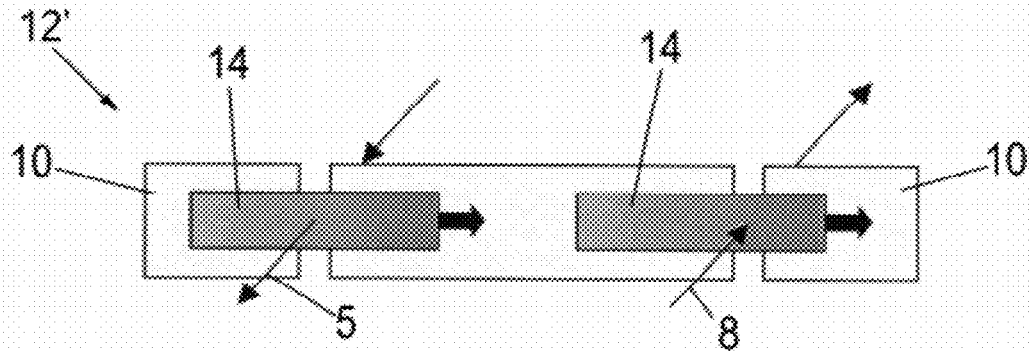
FIG. 5 is a schematic drawing illustrating a translatory filter arrangement of the instrument of FIG. 1 configured as two continuous filter strips.
Figure 7:
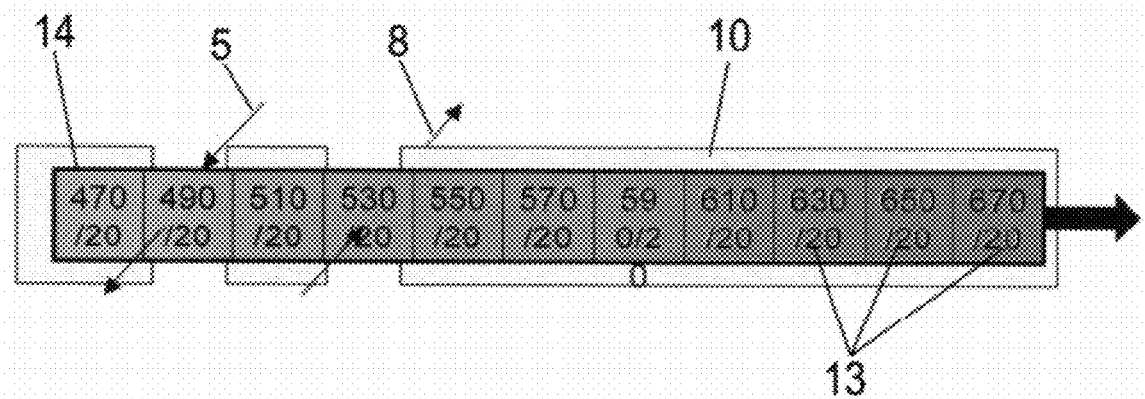
FIG. 7 is a schematic drawing illustrating various filter portions of the filter strips of FIGS. 5 and 6.

As illustrated in FIG. 5, the filter arrangement 9 (FIG. 1) of instrument 1 may be configured for translational movement. By way of example, the filter arrangement 9 (FIG. 1) may include a filter unit 12' (FIG. 5) comprising two one-piece filter strips 14 for example, such as a first filter strip 14 and a second filter strip 14, each of which having a non-continuous or discrete transmission spectrum. As illustrated in FIG. 7, each filter strip 14 may include a plurality of discrete filter portions 13 serially arranged with respect to each other. As shown, each filter strip 14 may include a row of discrete filter portions 13 having transmission maxima, for example at approximately 470, 490, 510, 530, 550, 570, 590, 610, 630, 650 and 670 nm. According to embodiments of the instant disclosure relating to dyes having a Stokes shift of about 40 nm, wherein the emission peak of one dye essentially corresponds to the excitation peak of another dye, a pair of first and second portions 13 related to one dye is formed by two distinct filter portions, the first filter portion 13 being provided by the first filter strip 14 and the second filter portion 13 being provided by the second filter strip 14.

Continuing with FIG. 5, each filter strip 14 may be operatively coupled to an individual drive 10 for translational movement. According to such embodiments, each filter strip 14 may be separately moved so that the first and second filter portions 13 of one pair of filter portions related to one dye can be moved in operative positions in which the first and second portions 13 are positioned in the excitation and emission beam paths 5, 8 while each other filter portion 13 is positioned outside the excitation and emission beam paths 5, 8.

Figure 6:
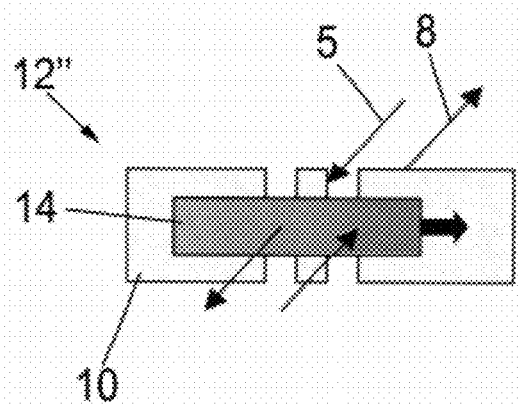
FIG. 6 is a schematic drawing illustrating another translatory filter arrangement of the instrument of FIG. 1 configured as one continuous filter strip.

With reference to FIGS. 6 and 7, in some embodiments, the filter arrangement 9 of instrument 1 may include a filter unit 12" comprising a single filter strip 14 having a discrete transmission spectrum. Being operatively coupled to only one drive 10, different dyes preferably, but not limited to having an at least approximately equal Stokes shift wherein the emission peak of one dye essentially corresponds to the excitation peak of another dye can be excited and detected by moving the filter strip 14 by equal moving steps. For example, as illustrated, first and second filter portions 13 being separated by one filter portion may be related to one dye. Accordingly, cross-talk can effectively be prevented.

Figure 8:
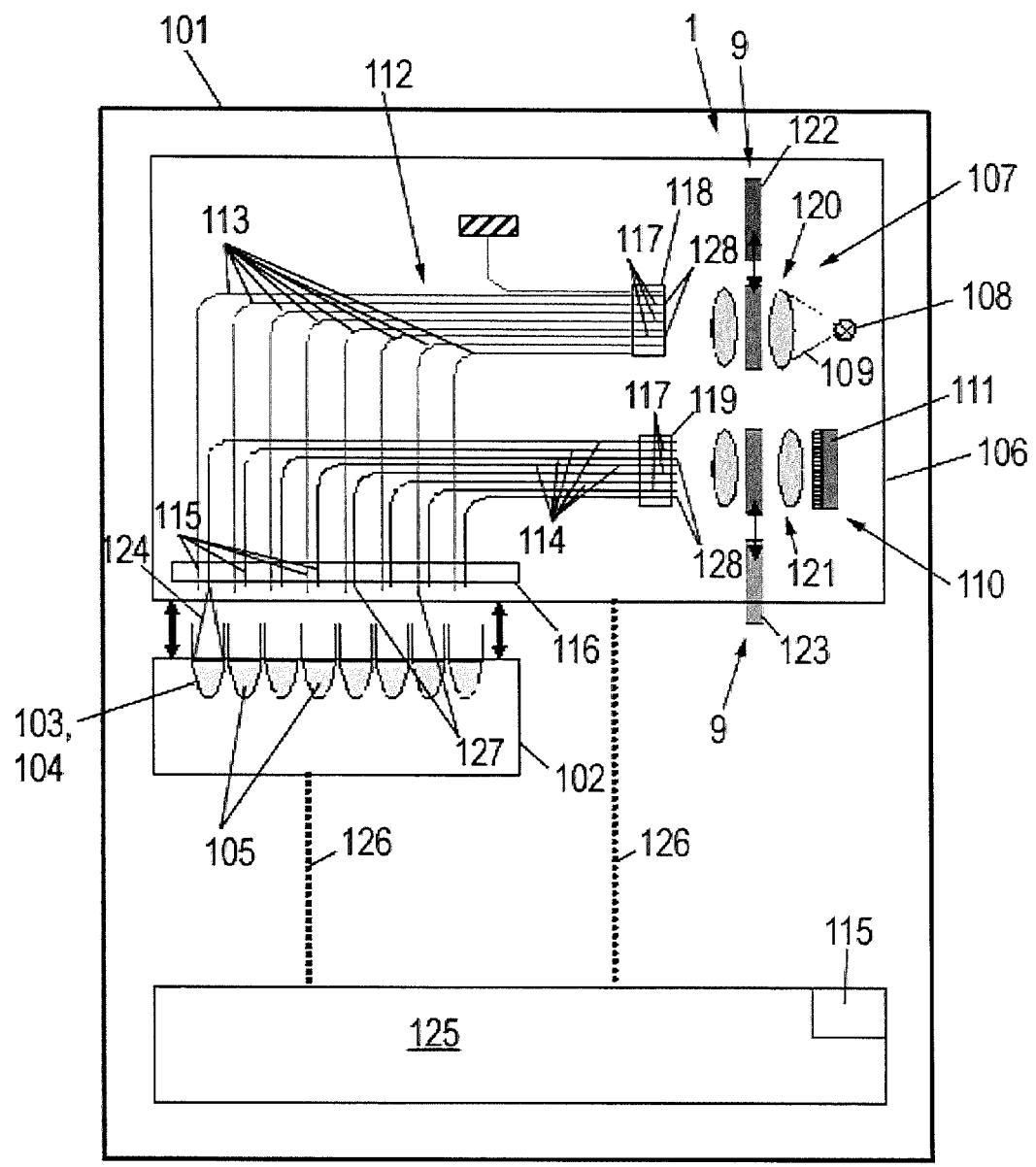
FIG. 8 is a schematic illustration of various modules of an exemplary system for the automated thermal treatment of samples comprising an instrument as depicted in FIGS. 1 to 7.

Now referring to FIG. 8, an exemplary system for the automated thermal treating of liquid samples generally referred to at reference numeral 101 comprising instrument 1 (as described and depicted in FIGS. 1-7 above) is provided. In some embodiments of the instant disclosure, instrument 101 may comprise a thermo-cycler for thermally cycling reaction mixtures of nucleic acids and one or more reagents through a series of temperature excursions (e.g., changes) and optically detecting the reaction products obtained by means of fluorescence. Instrument 101 may be used to perform the PCR, for example, such as real-time PCR or any other reaction of the nucleic acid amplification. According to specific embodiments of the present disclosure, instrument 101 may be used for the optical on-line detection of PCR reaction products and/or the isothermal treatment or execution of melting curves.

In some embodiments, instrument 101 may include various modules which are functional and (optionally) structural entities for treating liquid samples. For example, instrument 101 may include a thermal module 102 which can be brought in thermal communication with a multiwell plate 103 provided with plural cavities or wells 104 for receiving liquid samples 105. Thermal module 102 can thus serve as a mount supporting the multiwell plate 103. Additionally, thermal module 102 can be heated or cooled according to pre-defined temperature profiles so as to transfer heat in a controlled manner to/from the samples 105. A detection module 106 may also be used to detect light so as to identify reaction products which can be obtained as a result of a polymerase chain reaction of the samples 105, for example, wherein instrument 101 can be used for the optical on-line detection of the reaction products during progress of the amplification reactions. As indicated by the double arrows (FIG. 8), the detection module 106 may be moved in a controlled manner relative to the thermal module 102, e.g., moved vertically by means of a driven rack and pinion mechanism or any other mechanism enabling a vertical movement of detection module 106. According to such embodiments, the detection module 106 may be moved in a lowered first position adapted for optically detecting reaction products obtained from the samples 105 or in a raised second or loading/unloading position adapted for loading or unloading the instrument 101 with the multi-well plate 103.

According to embodiments of instrument 101, detection module 106 may include an excitation arrangement 107 having at least one light source 108 for generating excitation light 109 adapted to excite the emission of light 124 (e.g. fluorescence light), in the following denoted as "emitted light", of the samples 105. As illustrated, detection module 106 includes a detection arrangement 110 provided with at least one detector 111 for optically detecting the emitted light 124. Detection module 106, as illustrated, further includes a coupling arrangement generally referred to at reference numeral 112 for optically coupling each of the excitation arrangement 107 and the detection arrangement 110 to the wells 104. According to some embodiments, the coupling arrangement 112 may include a plurality of first optical fibers 113 (denoted as "excitation fibers") for transmitting excitation light 109 from excitation arrangement 107 to wells 104, and a second plurality of optical fibers 114 (denoted as "emission fibers") for transmitting emitted light 124 from wells 104 to detection arrangement 110. According to the illustrated embodiment, each well 104 of the multi-well plate 103 may be related to an individual pair of one excitation fiber 113 and one emission fiber 114.

As further illustrated in FIG. 8, well-sided first end portions 115 of the excitation fibers 113 are fixed with respect to each other by means of a first fixing element 116, while second end portions 117 of the excitation fibers 113 opposite the first end portions 115 thereof are fixed with respect to each other by a second fixing element 118. In some embodiments, well-sided first end portions 115 of the emission fibers 114 are fixed with respect to each other by means of the first fixing element 116, while second end portions 117 of the emission fibers 114 opposite the first end portions 115 thereof are fixed with respect to each other by a third fixing element 119. For example, the excitation light 109 can be coupled into the excitation fibers 113 at second end faces 128 and be coupled out of the excitation fibers 113 at first end faces 127 thereof. Additionally, the emitted light 124 may be coupled into the emission fibers 114 at first end faces 127 and be coupled out of the emission fibers 114 at second end faces 128.

Remaining with FIG. 8, excitation optics generally referred to at reference numeral 120 may be used to optically couple (e.g., introduce to, present or transfer) the excitation light 109 into the excitation fibers 113 at the second end faces 128. For example, one or more excitation filters 122 which are components of a filter arrangement 9 (as described and depicted with FIGS. 1-7 above) are used for filtering one or more specific wavelengths, or one or more ranges of wavelengths, before the excitation light 109 is coupled into the excitation fibers 113. In some embodiments in which the detection module 106 is in operative position, for example, the first end faces 127 of the excitation fibers 113 may be arranged in such a manner that the excitation light 109 is directed into the wells 4 to excite the emitted light 124 by the samples 105.

Continuing with FIG. 8, according to embodiments in which the detection module 106 is in operative position, the first end faces 127 of the emission fibers 114 may be arranged in such a manner that the emitted light 124 can be coupled into the emission fibers 114. For example, an emission optics generally referred to at reference numeral 121 may be used to optically couple the emitted light 124 leaving the emission fibers 114 at the second end faces 128 to the detector 111. One or more emission filters 123 which may be components of a filter arrangement 9 (described and depicted with FIGS. 1-7 above) may be used for filtering one or more wavelengths or one or more ranges of wavelengths from the emitted light 124 before the emitted light 124 hits the detector 111.

According to embodiments of the instant disclosure, controller 125 may be used for controlling the automated thermal treating of the samples 105. In some embodiments, controller 125 may comprise a micro-controller running a computer-readable program provided with instructions to perform operations in accordance with a pre-defined sequence of steps. For example, controller 125 may receive information from the various components of the system 101, such as from the detector 111, and generate and transmit corresponding control signals to the components which require control. As schematically illustrated in FIG. 8, electric lines 126 may be used for transmitting the electric signals.

All publications, patents and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An instrument for detecting an emission light emitted from one or more of a plurality of luminescence labels associated with an analyte in a sample, comprising:
    a mount configured to support a vessel for housing one or more samples;
    a light source capable of generating an excitation light for exciting said plurality of luminescence labels associated with said analyte in one or more samples housed in said vessel;
    an excitation arrangement configured to propagate said excitation light along an excitation beam path positioned between said light source and said vessel, said excitation beam path comprising one or more excitation light fibers configured to transmit said excitation light to said vessel;
    a detector capable of detecting said emission light emitted from one of said plurality of luminescence labels;
    a detection arrangement configured to propagate said emission light along an emission beam path positioned between said vessel and said detector, said emission beam path comprising one or more emission light fibers configured to transmit said emission light to said detector;
    a filter wheel rotatably mounted to a wheel hub, thereby defining a spin axis, said filter wheel comprising a plurality of filter portion pairs positioned around said wheel hub, each pair relating to one of said plurality of luminescence labels and comprising a first filter portion adapted to filter wavelengths of said excitation light and transmit said excitation light for exciting the related luminescence label, and a second filter portion adapted to filter wavelengths of said emission light and transmit said emission light emitted by said related luminescence label, said first filter portion of one of said plurality of pairs comprising said second filter portion of another of said plurality of pairs, said plurality of filter portion pairs being positioned around said wheel hub such that, upon rotation of the filter wheel about the spin axis, one of said plurality of pairs can be brought into an operative orientation relative to said excitation and emission beam paths such that said first filter portion is positioned in said excitation beam path and said second filter portion is positioned in said emission beam path.

2. The instrument according to claim 1, further comprising a carrier drive operatively connected to the filter wheel and wheel hub and adapted to rotate said filter wheel about said spin axis relative to said excitation and emission beam paths.

3. The instrument according to claim 2, wherein said filter portions are arranged in a manner that one of said plurality of pairs can be moved in said operative orientation by moving said filter wheel by equal rotation steps with respect to said excitation beam path and said emission beam path being stationary.

4. The instrument according to claim 1, wherein said filter wheel includes at least one opaque region adapted to inhibit the transmission of said emission light emitted by one of said plurality of luminescence labels, said opaque region arranged to be positioned in said emission beam path.

5. The instrument according to claim 1, comprising a one-piece filter for providing said first and second filter portions.

6. The instrument according to claim 5, wherein said one-piece filter has a discrete transmission spectrum.

7. A system for detecting an emission light emitted from one or more of a plurality of luminescence labels associated with an analyte in a sample, comprising:
    a mount configured to support a vessel for housing one or more samples and comprising a temperature-controlled block for heating said vessel comprising said one or more samples;
    a light source capable of generating an excitation light for exciting at least one of said plurality of luminescence labels associated with said analyte in said one or more samples;
    an excitation arrangement configured to propagate said excitation light along an excitation beam path positioned between said light source and an analyte region, said excitation beam path comprising one or more excitation light fibers configured to transmit said excitation light to said vessel;
    a detector capable of detecting an emission light emitted from one of said plurality of luminescence labels;
    a detection arrangement configured to propagate said emission light along an emission beam path positioned between said vessel and said detector, said emission beam path comprising one or more emission light fibers configured to transmit said emission light to said detector;
    a filter wheel rotatably mounted to a wheel hub, thereby defining a spin axis, said filter wheel comprising two or more pairs of filter portions positioned around said wheel hub, each pair of filter portions being related to one luminescence label and comprising a first filter portion adapted to filter wavelengths of said excitation light and transmit said excitation light for exciting said related luminescence label, and a second filter portion adapted to filter wavelengths of said emission light and transmit said emission light emitted by said related luminescence label, wherein said first filter portion of one pair is said second filter portion of another pair, said filter wheel being movable such that, upon rotation of the filter wheel about the spin axis, one of said pairs are brought into an operative orientation relative to said excitation and emission beam paths such that said first filter portion is in said excitation beam path and said second filter portion is in said emission beam path;

a carrier drive operatively connected to the filter wheel and wheel hub and adapted to rotate said filter wheel about said spin axis relative to said excitation beam path and said emission beam path;

and wherein a controller is configured to control activity of said carrier drive in a manner to move one of said pairs of said first and second filter portions in to said operative orientation.

8. The instrument of claim 1 wherein the excitation arrangement comprises one or more additional elements selected from the group consisting of lenses, planar mirrors, bent mirrors, transmission gratings, reflective gratings, prisms, and combinations thereof.

9. The instrument of claim 1 wherein the detection arrangement comprises one or more additional elements selected from the group consisting of lenses, planar mirrors, bent mirrors, transmission gratings, reflective gratings, prisms, and combinations thereof.

10. The system of claim 7 wherein the excitation arrangement comprises one or more additional elements selected from the group consisting of lenses, planar mirrors, bent mirrors, transmission gratings, reflective gratings, prisms, and combinations thereof.

11. The system of claim 7 wherein the detection arrangement comprises one or more additional elements selected from the group consisting of lenses, planar mirrors, bent mirrors, transmission gratings, reflective gratings, prisms, and combinations thereof.

* * * * *